United States Patent [19]

Davis

[11] 4,292,298

[45] Sep. 29, 1981

[54] PHARMACEUTICAL COMPOSITIONS CONTAINING PARACETAMOL

[75] Inventor: Adrian F. Davis, Dorking, England

[73] Assignee: Beecham Group Limited, England

[21] Appl. No.: 186,767

[22] Filed: Sep. 12, 1980

[30] Foreign Application Priority Data

Sep. 14, 1979 [GB] United Kingdom ............... 31925/79

[51] Int. Cl.$^3$ .......................... A61K 9/22; A61K 9/52; A61K 31/165; A61K 31/375
[52] U.S. Cl. .......................................... 424/10; 424/12; 424/22; 424/32; 424/33; 424/35; 424/37; 424/38; 424/280; 424/324
[58] Field of Search .............................. 424/10, 19–22, 424/32–38, 280, 320, 324

[56] References Cited

U.S. PATENT DOCUMENTS

| | | | |
|---|---|---|---|
| 2,953,497 | 9/1960 | Press | 424/38 X |
| 3,247,065 | 4/1966 | Koff | 424/38 X |
| 3,265,629 | 8/1966 | Jensen | 424/38 X |
| 3,446,891 | 5/1969 | Cavalli et al. | 424/35 X |
| 3,780,195 | 12/1973 | Balassa | 424/35 X |
| 3,860,733 | 1/1975 | Morse et al. | 424/35 X |
| 4,036,948 | 7/1977 | Kitamori et al. | 424/35 X |

FOREIGN PATENT DOCUMENTS 1292783 4/1969 Fed. Rep. of Germany .
2706705 2/1978 Fed. Rep. of Germany .
2081065 1/1972 France .

OTHER PUBLICATIONS

Houston et al., J. Pharm. Sci. 65(8): 1218–21, Aug. 1976, Drug Biotransformation Interaction in Man VI Acetaminophen and Ascorbic Acid.
Raghuram et al., Toxicol. Lett. 1978 2(3): 175–178, Effect of Vitamin C on Paracetamol Hepatotoxicity.
Subaschandran et al., Poultry Sci. 46(5): 1073–6 (1967), Acetyl-p-aminophenol and Vitamin C in Heat Stressed Birds.
Sacharin Int. J. Vitamin Nutr. Res. (1977) 47(1): 68–74, Blood Levels and Bioavailability of Ascorbic Acid After Adm. of a Sustained Release Formulation to Humans.
Kassem, Bull. Fac. Pharm., Cairo U., 1973, Pub. 1975, 12(2): 11–24, Microencapsulation of L-Ascorbic Acid.

*Primary Examiner*—Shep K. Rose
*Attorney, Agent, or Firm*—Jacobs & Jacobs

[57] ABSTRACT

The acute liver toxicity effects of paracetamol are reduced by co-formulating with sustained release ascorbic acid which produces high liver concentrations of ascorbate anion after oral administration of the co-formulation. A suitable form of sustained release ascorbic acid is prepared by microencapsulation of particles of ascorbic acid in membranes which act as microdialysis cells.

10 Claims, No Drawings

PHARMACEUTICAL COMPOSITIONS CONTAINING PARACETAMOL

This invention relates to pharmaceutical compositions having analgesic and antipyretic activity, and more particularly, to compositions comprising paracetamol and ascorbic acid.

Paracetamol (p-hydroxyacetanilide) is an analgesic and antipyretic agent which is widely used in prescription and non-prescription medicines, often in combination with other biologically active compounds such as caffeine and acetylsalicylic acid. When administered at the recommended dosage regimen it is generally believed to be a safe and effective therapeutic agent without significant undesirable side effects. However, if the usual recommended single doses are exceeded, severe and often fatal liver damage can occur. Indeed, suicide by paracetamol poisoning has become a major cause for concern. Moreover, there are indications that chronic dosing even at the recommended levels can result in liver damage.

It is believed that the liver toxicity of paracetamol is due to the covalent binding of a paracetamol metabolite to vital liver cell macromolecules. At the recommended dose levels, the metabolite appears to be effectively removed by biochemical processes, but at excessive dose levels, these biochemical processes become depleted and the excess metabolite exerts its toxic effects.

This invention is based on the discovery that a sufficient concentration of ascorbate anion in the liver can prevent or at least mitigate the toxic effects of excessive paracetamol on the liver (centrilobular hepatic necrosis). Unfortunately, ascorbic acid when administered alone is incapable of producing the required concentration/time profile of ascorbate anion in the liver to have this antidote effect. The difficulty lies in the fact that absorption of ascorbate through the gastrointestinal wall is not linearly related to dose and in the fact that ascorbate rapidly disappears from the liver after achieving a peak concentration. Progressively higher oral doses of ascorbic acid produce smaller and smaller increases in ascorbate concentration in the liver and do not markedly affect the duration in the liver. The effective maximum concentration and duration of ascorbate, achieved after oral dosing of very large amounts of ascorbic acid is, we have found, less than that required to act as an antidote to acute paracetamol liver toxicity. The aim of the present invention is to overcome or at least reduce this problem by increasing the duration of ascorbate ions in the liver by using ascorbic acid in a sustained release form.

According to the present invention there is provided an analgesic and antipyretic pharmaceutical composition suitable for oral administration, comprising paracetamol and a sufficient amount of ascorbic acid in a sustained release form, to counteract the potential liver toxicity effects of the paracetamol. Preferably, the ascorbate anion content is from 30% to 100% by weight of the paracetamol content. The sustained release forms can involve a wide variety of physical modifications of ascorbic acid. For example, the solid ascorbic acid may have a coating which is not readily water-soluble but which is slowly attacked and removed by water, or through which water can permeate.

Alternatively, the acid can be distributed throughout a support matrix which is not readily water soluble but which, like the above-mentioned coating, is slowly attacked and removed by water or can be permeated by water. Such modifications are generally well known to those skilled in the art, and do not in themselves form part of the present invention. Spray-dried ascorbic acid also has been found to have sustained release properties, and the present invention encompasses this form of acid.

Preferably, the composition of the invention is provided in unit dosage form, and each unit dose may contain from 300 mg to 1000 mg of sustained release ascorbic acid.

On particular form of sustained release ascorbic acid comprises particles of ascorbic acid coated with different thicknesses of hydrophobic coating materials such as beeswax, glycerylmonostearate, stearic acid or cetostearyl alcohol. A silicon coating can also be used. A mixture of such particles having coatings of different thicknesses provides a timed release of ascorbic acid when swallowed. Such a mixture of particles is conveniently carried in a conventional gelatine capsule for oral administration. In one example of a composition of the invention, paracetamol would be included together with the mixed coated ascorbic acid particles in a gelatine capsule.

Another particular form of sustained release ascorbic acid may be prepared by granulation of the powdered ascorbic acid, together with various hydrophobic excipients to produce a hydrophobic matrix with the ascorbic acid distributed throughout. The matrix may contain from 50 to 99% by weight of ascorbic acid, preferably from 75 to 99%. When swallowed, gastric fluid penetrates the matrix and, over a prolonged period, the ascorbate is leached out. The timing of the release is controlled by varying the pore size of the matrix. Suitable hydrophobic matrices are provided by fats and waxes or synthetic or natural resins such as polyvinyl chloride, polyethylene, vinyl acetate/vinyl chloride copolymer, sandarac resin or copal resin. The tiny granule matrices produced by these methods can be compressed into tablets together with conventional tabletting excipients or can be carried in conventional gelatine capsules. In the latter case, an example of a composition of the invention would comprise a capsule filled with paracetamol and a plurality of such matrices. In the case of a tablet the paracetamol content might be present in one layer and the compressed matrices containing ascorbic acid in another. Multi-layer tablets for sustained release are, of course, well known per se.

Yet another form of sustained release ascorbic acid is prepared by microencapsulation of particles of ascorbic acid in membranes which act as microdialysis cells, i.e. gastric fluid permeates the microcapsule walls, swells the microcapsule and the ascorbate dialyses out. One commercially available sustained release ascorbic acid of this kind consists of microcapsules having membranes of acacia gum/gelatine/ethyl alcohol. This commercial product is available from Eurand Limited (France) under the trade name "Diffucaps". Again, as an example of a composition of the invention embodying this kind of sustained release ascorbic acid, the microcapsules might be carried, together with the paracetamol in a conventional gelatine capsule. Such a capsule may contain from 20 to 50% by weight of microcapsules and 50 to 80% by weight of paracetamol. Alternatively the microcapsules could be tabletted together with an efficient tablet disintegrant.

A further sustained release form of ascorbic acid is enteric coated ascorbic acid. As such formulations release ascorbic acid only in the alkaline conditions of the intestine, release is sustained by prolonged gastric emptying or, when used in overdose, the large amount of acid release buffers the intestinal contents to less basic pH slowing further release.

Enteric coatings are well known in the art. Suitable coatings include cellulose acetate phthalate coatings (e.g. Eudragit).

The liver concentrations of ascorbate following the oral administration of a particular sustained release ascorbic acid may be monitored by analysis of liver samples taken from killed laboratory animals being dosed with the compound. In this way any particular sustained release ascorbic acid can be evaluated to determine its concentration-with-time profile in the liver and comparison can then be made with the concentration/time profile of ascorbic acid by itself. Furthermore, there is a direct relationship with blood plasma levels of ascorbate and liver concentrations. Therefore, in human beings the concentration-with-time ascorbate profile in the liver can be inferred from blood concentration measurements.

It is believed that the greater the concentration of ascorbate in the liver relative to paracetamol or paracetamol metabolite the greater the protection against liver damage, up to the point, of course, when complete protection is achieved. Some protection appears to be achieved when the concentration of ascorbate:paracetamol in the liver is 1:8 but higher concentrations of ascorbate than this are needed for good or substantially complete protection. Accordingly, in the compositions of this invention it is preferred that the weight ratio of sustained release ascorbate:paracetamol should be capable of producing corresponding liver concentrations of at least 1:8, preferably at least 1:4, more preferably at least 1:2 ascorbate:paracetamol. It is envisaged that the theoretical ascorbate anion content of the compositions of the invention will preferably be at least 30% by weight of the paracetamol content and more often will be at least 70%, or even up to 100% of the paracetamol content.

Since the compositions of this invention are intended for oral administration, any of the usal oral dosage forms of pharmaceutical compositions may be adopted. Thus the compositions may be in the form of capsules, tablets, pills, dragees or powders for mixing with orally consumable liquids, or liquid syrups. The compositions may include the carriers and excipients conventional in such oral dosage forms. Excipients which may be present include colouring and flavouring materials.

A singleunit dosage of the compositions of the present invention will normally contain from 250 mg to 1000 mg of paracetamol with the proviso that the unit dosage should not be so large as to make swallowing difficult.

Despite the reduced potential for liver toxicity of compositions of the present invention it is envisaged that they may be offered to the consumer with the contraindications and instructions as to recommended dose conventional in paracetamol formulations.

In another aspect of the present invention there is provided a method of reducing the potential liver toxicity effect of a pharmaceutical composition comprising paracetamol, which method comprises including in said composition a sustained release ascorbic acid, as discussed above.

In another aspect of the present invention there is provided a method of reducing paracetamol induced liver damage which comprises the oral co-administration of paracetamol and sustained release ascorbic acid, as discussed above. The paracetamol and sustained release ascorbic acid may be administered together or consecutively.

In another aspect of the present invention there is provided a treatment pack comprising an oral dosage unit comprising paracetamol and an oral dosage unit comprising sustained release ascorbic acid, as discussed above, these two oral dosage units being retained in said pack in association with one another, e.g. by blister packing the two dosage units in the same blister.

The following Example illustrates the present invention:

EXAMPLE

The protective effect of a sustained release ascorbic acid against paracetamol liver toxicity was assessed at several dose levels in groups of twenty mice. It had previously been shown that an oral dose of 450 mg/kg produced moderate liver damage in mice with approximately 35% mortality. In the experiment the assessment of liver damage was by measurement of liver weight increases, which had been shown to be proportional to liver toxicity and by direct histological examination of the liver. The mice were dosed by intubation directly to the stomach.

Results:

| Treatment | Increase in mean rel. liver weight (gms) | Mean necrosis score |
|---|---|---|
| Vehicle Control | 0 | 0 |
| Paracetamol alone (450 mg/kg) | 1.9 | 7.5 |
| Paracetamol (450 mg/kg) + 300 mg/kg sustained release ascorbic acid (Eurand) | 0.6 | 2.9 |
| Paracetamol (450 mg/kg) + 600 mg/kg sustained release ascorbic acid (Eurand) | 0.3 | 0.67 |

These results indicate that sustained release ascorbic acid reduces liver toxicity (as measured by increase in liver weight and by direct histological examination at the dosage tested).

The lack of protective effect of non-sustained-release ascorbic acid is shown by the same method. The results being as follows:

| Treatment | Increase in mean rel. liver weight (gms) | Mean necrosis score |
|---|---|---|
| Paracetamol (450 mg/k) + Ascorbic acid 300 mg/kg | 2.22 | 7.86 |

I claim:

1. An analgesic and antipyretic pharmaceutical composition suitable for oral administration, comprising paracetamol, characterised in that the composition further includes a sufficient amount of ascorbic acid in a sustained release form to counteract the potential liver toxicity effects of the paracetamol.

2. A composition according to claim 1, in which the ascorbate anion content is from 30% to 100% by weight of the paracetamol content.

3. A composition according to claim 1, in which the weight ratio of sustained release ascorbate:paracetamol is capable of producing corresponding liver concentrations of at least 1:8 of ascorbate:paracetamol.

4. A composition according to claim 1, in unit dosage form.

5. A composition according to claim 4, containing from 300 mg to 1000 mg of sustained release ascorbic acid per unit dose.

6. A composition according to claim 5, containing from 250 mg to 1000 mg of paracetamol per unit dose.

7. A composition according to claim 4, in the form of tablets, pills, capsules, dragees, a powder or syrup.

8. A composition according to claim 1, in which the sustained release ascorbic acid is in the form of solid ascorbic acid having a water resistant or water permeable coating, or spray dried ascorbic acid, or a hydrophobic matrix having ascorbic acid particles distributed throughout, or enteric coated ascorbic acid.

9. A treatment pack comprising an oral dosage unit comprising paracetamol and an oral dosage unit comprising sustained release ascorbic acid, the two oral dosage units being retained in the pack in association with one another.

10. A method of reducing the potential liver toxicity effect of a pharmaceutical composition comprising paracetamol, in which an effective amount of ascorbic acid in sustained release form is included in the composition.

* * * * *